United States Patent
Horigane (10) Patent No.: US 6,537,826 B1
(45) Date of Patent: Mar. 25, 2003

(54) PROCESS FOR MATERIAL PREPARATION, APPARATUS THEREFOR AND METHOD FOR ANALYSIS

(75) Inventor: Akira Horigane, 16-520-201, Matsushiro 5-Chome, Tsukuba-Shi, Ibaraki 305-0035 (JP)

(73) Assignees: Akira Horigane, Tsukuba (JP); National Agricultural Research Organization, Tsukuba (JP)

( * ) Notice: Subject to any disclaimer, the term of this patent is extended or adjusted under 35 U.S.C. 154(b) by 81 days.

(21) Appl. No.: 09/762,416
(22) PCT Filed: Sep. 6, 2000
(86) PCT No.: PCT/JP00/06029
§ 371 (c)(1), (2), (4) Date: Feb. 6, 2001
(87) PCT Pub. No.: WO01/18527
PCT Pub. Date: Mar. 15, 2001

(30) Foreign Application Priority Data

Sep. 7, 1999 (JP) ............................................. 11-253592

(51) Int. Cl.$^7$ ................................................. G01N 1/42
(52) U.S. Cl. ........................... 436/176; 83/15; 83/452; 422/99; 422/102; 422/104; 436/174
(58) Field of Search ................................ 436/174, 176; 422/102, 104, 99; 427/2.11, 2.13, 4; 83/15, 167, 452

(56) References Cited

U.S. PATENT DOCUMENTS

| | | | |
|---|---|---|---|
| 5,533,342 A | * | 7/1996 | Gordon |
| 5,844,092 A | * | 12/1998 | Presta et al. |
| 6,098,410 A | * | 8/2000 | Horigane |

* cited by examiner

*Primary Examiner*—Jan Ludlow
(74) *Attorney, Agent, or Firm*—Flynn, Thiel, Boutell & Tanis, P.C.

(57) ABSTRACT

An apparatus and a process for preparing a material, such as a sample, for analysis, observation, recording or the like, at a high accuracy, by a simple construction and simple operation, which can form a cut face and/or a cut rift while preventing deformation, destruction and denaturing of the material. The process involves embedding a part of the material (11) in a filler (13) in a holder (4) of a holding unit (1) under settling with a settling means (5), holding the protruding portion (11b) of the material (11) by a protruding portion support (7) of a mount (2), freezing the material (11) instantaneously by dry ice placed in dry ice wells (6a, 6b) while effecting a gas phase replacement and cutting the material (11) by a cutter (22) to form a cut face (14) and/or a cut rift (15).

10 Claims, 5 Drawing Sheets

PROCESS FOR MATERIAL PREPARATION, APPARATUS THEREFOR AND METHOD FOR ANALYSIS

FIELD OF THE INVENTION

The present invention relates to a process and apparatus for material preparation and to a method for analysis therewith, by processing a material by forming a cut face and/or a rift therein, in particular, for preparing a sample which serves advantageously for analysis, observation, record or the like (in the following, denoted sometimes as analysis etc.). More particularly, the present invention relates to a process and apparatus for material preparation adapted especially to deal with materials which are subject to deformation, destruction and denaturing, including biological objects, organic and inorganic substances, chemical products and so on, as well as to a method for analysis therewith.

BACKGROUND OF THE INVENTION

For subjecting a material, especially among those, for example, biological bodies, such as plant seeds, and others, as a sample to a spectroanalysis, it is necessary to prepare a mirror-finished cut face of the material. On the other hand, for examining a sample by mass spectrometry by penetrating through the sample with a laser beam, the sample should be cut to form a slice of a specific thickness. For the device for preparing such a mirror-finished face of a sample by forming therein a cut face and/or a rift, a sliding cutter or a rotary cutter is used.

A sliding cutter operates by sliding a sharp blade and is adapted for slicing, for example, an animal tissue, such as liver, embedded in a soft substance, such as paraffin. However, the sliced tissue is apt to be deformed or destroyed by the pressure of the cutter blade. In particular, in the case of slicing a tissue, such as a stalk or a leaf, of a plant, which contains silica components, such as plant opal, the steel knife may be nicked by such silica and scars, such as knife marks, may be left on the resulting sliced sample.

A rotary cutter operates with a rotary cutting element, such as a diamond saw, which may encounter a similar disadvantage of deformation and destruction of the tissue by the cutter pressure as in the sliding cutter mentioned above, with a further defect that the cut sample is apt to suffer from denaturing due to the frictional heat upon cutting. For evading such a defect, cutting oil is used for the purpose of cooling and prevention of oxidation. In the case of a biological sample, cutting oil is absorbed in the cut sample easily and is detected upon the spectroanalysis as a contaminant component, reducing the analysis accuracy.

In both cutter arrangements, the material to be cut is fixedly held by embedding it in, for example, a paraffin wax or a resin, in order to immobilize the material upon cutting, which may cause also a decrease in the accuracy of the analysis by a possible interminglement of such holding material into the cut sample upon cutting.

A first object of the present invention is to provide a process for material preparation in which a material can be processed by forming a cut face and/or a rift therein while preventing deformation, destruction and denaturing of the material in a simple way using an apparatus of simple construction.

A second object of the present invention is to provide a process for material preparation in which a material can be processed by forming a cut face and/or a rift therein and preparing an examination surface at a predetermined position and at a definite angle of inclination while preventing deformation, destruction and denaturing thereof in a simple way, so as to obtain a sample to be examined by analysis, observation, recording or the like at a high accuracy, using an apparatus of simple construction.

A third object of the present invention is to provide a material preparing apparatus adapted for realizing such a material preparation as above.

DISCLOSURE OF THE INVENTION

The present invention resides in the following process and apparatus for performing the material preparation:
(1) A process for effecting preparation of a material, comprising
  fixing the material on a holding unit,
  freezing the material with dry ice, while replacing the gas-phase with the evolved carbon dioxide gas and
  cutting the material by a cutter so as to form a cut face and/or a cut rift.
(2) The process as defined in the above (1), wherein the material is embedded in a filler filled in the holding unit and the filler is frozen in this state by dry ice to solidify, before the material is cut by the cutter.
(3) The process as defined in the above (1) or (2), wherein the cut surface, resulting after the cut face and/or the cut rift is formed by the cutter, is polished by the cutter to attain a mirror surface finishing.
(4) The process as defined in any one of the above (1) to (3), wherein the material is a sample for analysis, observation or recording.
(5) A material prepared by the process as defined in any one of the above (1) to (4).
(6) An apparatus for effecting material preparation comprising
  a holding unit having one or more holders,
  a settling means for settling the material held in the holder,
  dry ice wells disposed so as to effect freezing of the material held in the holding unit and to effect a gas phase replacement and
  a cutting space for permitting the cutting of the material by a cutter in a state frozen by dry ice with a gas phase replacement to form a cut face and/or a cut rift.
(7) The apparatus as defined in the above (6), wherein a plurality of the holders are arranged in a row.
(8) The apparatus as defined in the above (6) or (7), wherein it further comprises a mount which has a support for supporting the protruding portion of the material protruding from the holding unit and which is disposed on the holding unit disengageably.
(9) The apparatus as defined in the above (8), wherein the mount has an affixing means for affixing the cut off protruding portion.
(10) A method for effecting analysis, in which the material as defined in the above (5) is used as the sample.

The material to be subjected to the material preparation according to the present invention is processed by forming a cut face and/or a cut rift therein. For such a material, every one subject to deformation, destruction and denaturing may be mentioned, wherefor especially materials for samples for analyses etc. are particularly adapted.

Such a material may be those of biological, organic and chemical origins. Specific examples thereof include seeds, stalks, leaves and roots of plants and tissues of plants and animals including human beings. They may be those for use in applications other than a sample. Materials other than the above include, for example, materials for slicing a wafer from a silicon crystal, easily deformable textiles and others.

Such analysis, observation and others using a sample obtained by the material preparation may comprise every practice of analysis, observation, recording and so on to be carried out on the cut face or on the cut rift of the sample, including those in which mathematical processing is employed, such as for example, spectroanalyses using electromagnetic wave (including IR spectroscopy, Raman spectroscopy, X-ray fluorometry and chromatic differential spectrophotometry) and mass spectrometry, and further, those in which observation, determination and recording of an image is included, such as for example, microscopy (including electromicroscopy), TV-image analysis, photography, visual inspection and so on.

According to the present invention, such a material subject to deformation, destruction or denaturing is held on a holding unit and the material is frozen substantially instantaneously by dry ice while replacing the ambient atmosphere by carbon dioxide gas, whereupon the material is cut to form a cut face and/or a cut rift to effect the material preparation. Dry ice is a solid product of carbon dioxide produced by cooling and compressing carbon dioxide gas, for which a product having a grain size of 0.1–5 mm, preferably 0.1–2 mm, may be employed. It is enough to place dry ice at a portion capable of cooling and freezing the material and replacing the ambient atmosphere with carbon dioxide gas, while it is preferable to place dry ice around and above the material so as to cover it.

The material should be held fixedly on the holding unit during the cutting thereof. The fixation of the material may be realized using a settling member arranged in the holding unit or by filling a filler in the holding unit and making use of the adhesion force of the filler itself or, further, by solidifying the material by cooling with dry ice. As the filler, a substance capable of solidifying at a lower temperature, such as a putty (for example, based on silicone or on aqueous acrylic resin) or water, may favorably be employed due to its better processability, while it is permissible to use a polymerized or condensed substance, such as a resin.

The holding unit may be constructed in such a manner that the material is held partly so as to protrude a part of the material out thereof and to fix the material by a settling means. It is enough that a holder formed in the holding unit is constructed so as to enable the holding of the material, but the holder may preferably have a form to match the contour of the material so as to permit the holding of the material after the cutting. However, the holder may not necessarily be constructed to correspond completely to the contour of the material and may preferably have a form somewhat larger but roughly adapted to the contour of the material and, by filling the holder with a filler, such as putty or water, to embed the material therein. The holder may preferably be provided in plural numbers, wherein it is efficient and favorable to arrange them in one or more rows within one and the same plane so as to enable cutting of the materials by one single action of the cutter simultaneously. When a plurality of rows of the holders are used, they may be arranged in a form of a lattice or honeycomb.

The settling means is a member serving to settle the material held in the holder and it may preferably comprise a resilient member arranged so as to permit the settling of the material held in the holder by pressing onto the material under such a pressure that no damage of the material is caused in accordance with the configuration held in the holder but the material is settled in a fixed state. The holder and the settling member may be provided in an integral form. If the holding unit is provided with a plurality of holders, the settling members are also disposed correspondingly. For example, when the holders are arranged in a row, the settling members may be constructed in a corresponding form, namely, they may be in a form of an elongated arm or in a comb-like form.

It is possible to use, as the settling member, a filler, so long as the construction of the holder permits. Thus, if the holder is constructed in a form of a cavity, the gap between the material inserted in the cavity and the cavity wall may be filled with a filler, such as a putty, whereupon the filler is caused to solidify to attain a firm fixation of the sample. For the filler, a sheet-formed one, such as both-sided sticky tape, may also be used.

Dry ice wells for accommodating dry ice for effecting freezing of the material held on the holding unit and gas phase replacement may be arranged in the holding unit integrally therewith or separately on a mount or in a portion between the mount and the holding unit. Dry ice may favorably be piled in the dry ice wells arranged in a form of a groove surrounding the holding unit and serve an anchoring function for preventing floating of dry ice particle due to the wind pressure caused by the action of cutter rotating at a high speed, while they may simply be piled around and above the holding unit.

A cutting space is arranged to permit cutting, by a cutter, the material held on the holding unit to form a cut face and/or a cut rift. The cutter is arranged in the holding unit integrally therewith or independently therefrom. In general, cutters in cutting arrangements, such as a high performance slicer for semiconductor wafers and so on, may be used as such, while a cutter using a cutting lever having the fulcrum at one end of the holding unit may also be used in a simple cutting. Here, the holding unit is assembled on the cutting arrangement under positioning so as to permit the cutting of the sample at a portion protruding from the holder. When a plurality of samples are put on a plurality of holders, they are disposed in such an arrangement that all the samples are cut at once and in the same plane. In the case of, for example, a plurality of holders arranged in a row, cutting of the materials is performed by causing the cutter of the holding unit to move in the direction of the row. For the cutter, any voluntary type including a sliding cutter and a rotary cutter may be used, while preference is given to a rotary cutter having cutting teeth of an ultrahard material, such as diamond, as represented by a diamond saw.

For cutting the material by a cutter at a portion protruding from the holding unit, it is preferable to install a support for supporting the material at its protruding free top. The support may favorably be provided with an affixing means, such as a sticky tape, so as to enable the affixing and recovery of the cut off protruding portion as a sample for chemical analysis. The protruding portion support may favorably be arranged on the holding unit directly or on the mount disengageably under intermediation by the setting mount or so on.

For the material preparation using the apparatus described above, the material is first held in the holder of the holding unit, preferably in a state embedded in a filler filled in the holder, and is settled by an assist of a settling member, if present. The settling of the material may be assisted by the protruding portion support disposed on the mount, if the mount is present, by resting the protruding portion of the material on it. Dry ice particles are then placed in the dry ice wells so as to heap the dry ice particles around and over the material.

Dry ice has a sublimation temperature of minus 78.5° C. at atmosphere pressure, so that the material will be frozen substantially instantaneously and the ambient atmosphere is replaced by inert carbon dioxide gas. Due to the instantaneous freezing of the material, there occurs no growth of ice crystals within the tissue and, in addition, due to the exclusion of oxygen, no denaturing by the influence of ice, oxygen and heat can be brought about. The material is fixed by solidification of the filler by the low temperature.

In this state, the cutter is slid or rotated in the cutting space to effect cutting of the material, whereby a cut face or a cut rift is formed on the so-cut material while the frictional heat is absorbed by dry ice so that the material is maintained under an inert atmosphere at a temperature of minus 78.5° C. Due to the solidified state of the material together with the filler, soft tissues, such as plant root and the like, can be cut and the cut fragments are scattered away without contaminating the cut face of the material. By shaving shallowly the cut face by the cutter blade, a mirror-finished surface can be obtained. Here, the cut and shaven fragments are removed by being captured in the dry ice and a uniform and contaminant-free mirror surface is formed on the material.

The so-prepared material is taken out from the holding unit and used for each specific purpose, while it may favorably be used as a sample for analysis or so on. The method of analysis according to the present invention is effected using the material given above as the sample for analysis or so on. When a sample for analysis or so on is prepared by forming a cut face and/or a cut rift on the material, the so-prepared sample may be taken off together with the sample holder from the mount and set as such on an analyzing apparatus for performing analysis, observation, recording and so on. These examination procedures may be performed either in the frozen state of the sample or in a state after the sample has been warmed to normal temperature in, for example, a desiccator, in order to prevent dew condensation. Samples having the cut face can be examined by analysis, such as a spectroanalysis, by irradiating the cut face with a beam of an electromagnetic wave, by observation under a microscope or with photography and by recording and measurements of the configuration etc. with an image processor or the like. When a cut rift is formed in the sample in the direction parallel to the cut face, an accurate mass spectroscopic analysis can be realized by vaporizing the constituent substances by irradiating the formed slice with a laser beam. Using such a sample, analysis of trace components, which has hitherto been impossible due to light scattering, can be realized, since the sample can be settled in a posture in which the cut face is vertical to the optical axis. The cut face can be formed in a plane at a definite distance from the front end of the sample holder, permitting thus a quantitative analysis of a number of samples under the same condition, whereby the analysis accuracy is increased. When a mirror surface is formed by shaving after the cut face or the cut rift has been prepared, light scattering is prevented and the analysis accuracy can further be increased.

Due to the condition of cutting of the material under a state frozen by dry ice, the sample does not suffer from deformation, destruction and denaturing and can be used for analysis or so on, so that analysis, observation and so on of the exact internal state of the sample are made possible with a high accuracy. An influence of carbon dioxide gas evolved from dry ice on the analysis accuracy can be minimized, since such gas can be removed easily.

There occurs no denaturing in the so-cut material and in the protruding portion thereof, since freezing occurs instantaneously, so that the original state can be restored after thawing. When a seed of a plant serves as the material, the embryo keeps its germing potential and, thus, is permitted to grow. Therefore, it is possible to select superior seeds by the sample analysis and to multiplicate contemplated seeds by cultivating such plants by growing from the embryos of the selected seeds. Here, selection of the seed can be attained without suffering from any influence by the analytical operation, by settling the seed in such a posture that its embryo is in the inside of the holder. The protruding portion cut off may be used as a sample for analyzing the composition thereof by chemical analysis or for other purposes. When the prepared material is used for other purposes than the sample for analyses, namely, for example, when silicon crystal is cut into a silicon wafer, the intrinsic components and physical and chemical properties before the preparation are retained, since no denaturing occurs.

According to the present invention, a material is cut under a condition in which the material is frozen with gas phase replacement by dry ice, so that a cut face and/or cut rift can be formed by a simple construction and simple operation while preventing deformation, destruction and denaturing of the material and, thus, a highly accurate analysis and so on can be realized when the prepared material is used for such analysis and so on.

When the holder is filled with a filler and the material is embedded therein and, then, the filler is frozen by dry ice, an easy fixation of the material can be realized and objects, of which fixation is not easy, such as seeds of plants, can easily be fixed.

By arranging a support for supporting the portion protruding from the holder, displacement of the material due to vibration etc. upon cutting by the cutter can be prevented and the material can be cut precisely. When the support is provided with an affixing means, the protruding portion cut off can be recovered and utilized effectively for analysis or so on.

BRIEF DESCRIPTION OF THE DRAWINGS

In the following, embodiments of the present invention will be described with reference to the drawings.

THE BEST MODE FOR EMBODYING THE INVENTION

In FIGS. 1 to 5, the material preparation apparatus 10 comprises a holding unit 1 and a mount 2 assembled disengageably by a joint means 3a. On the holding unit 1, a plurality of holders 4, each constituted by a recess of a form corresponding to the half part of the material 11 (a seed of wheat in this embodiment), are arranged in a row along the upper edge. A settling means 5 arranged in a comb-like form for putting down each material 11 held in the holder 4 at its portion 11a to be held is arranged by a joint means 3b. The holder 4 may preferably have a space 4a to be filled with a filler 13. In the holding unit 1, dry ice wells 6a in a form of grooves are disposed surrounding the holders 4 for receiving dry ice 12.

Figure 1:
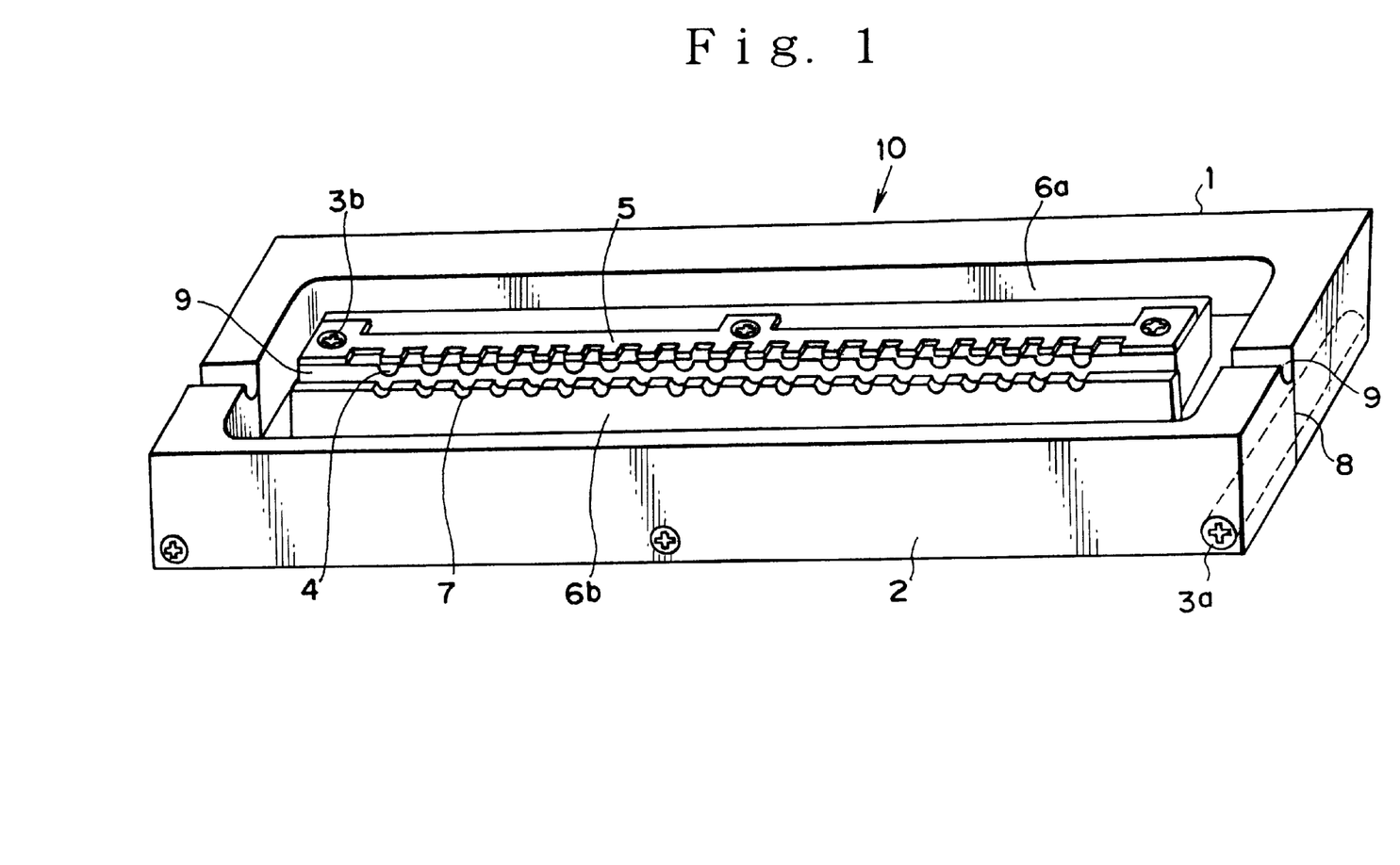
FIG. 1 shows an embodiment of the apparatus for material preparation in a perspective view.

The mount 2 is arranged in combination with the holding unit 1 disengageably therefrom, wherein the supports 7 for supporting the protruding portion 11b of the material 11 are arranged in a row so as to confront the holders 4. On each top end of the supports 7, an affixing means 7a constituted of a both-sided sticking tape for capturing the protruding portion 11b is disposed. Around the supports 7, a dry ice well 6b is arranged, which continues to the dry ice well 6a.

Above the junction interface 8 between the holding unit 1 and the mount 2, a cutting space 9 is disposed.

Figure 2:
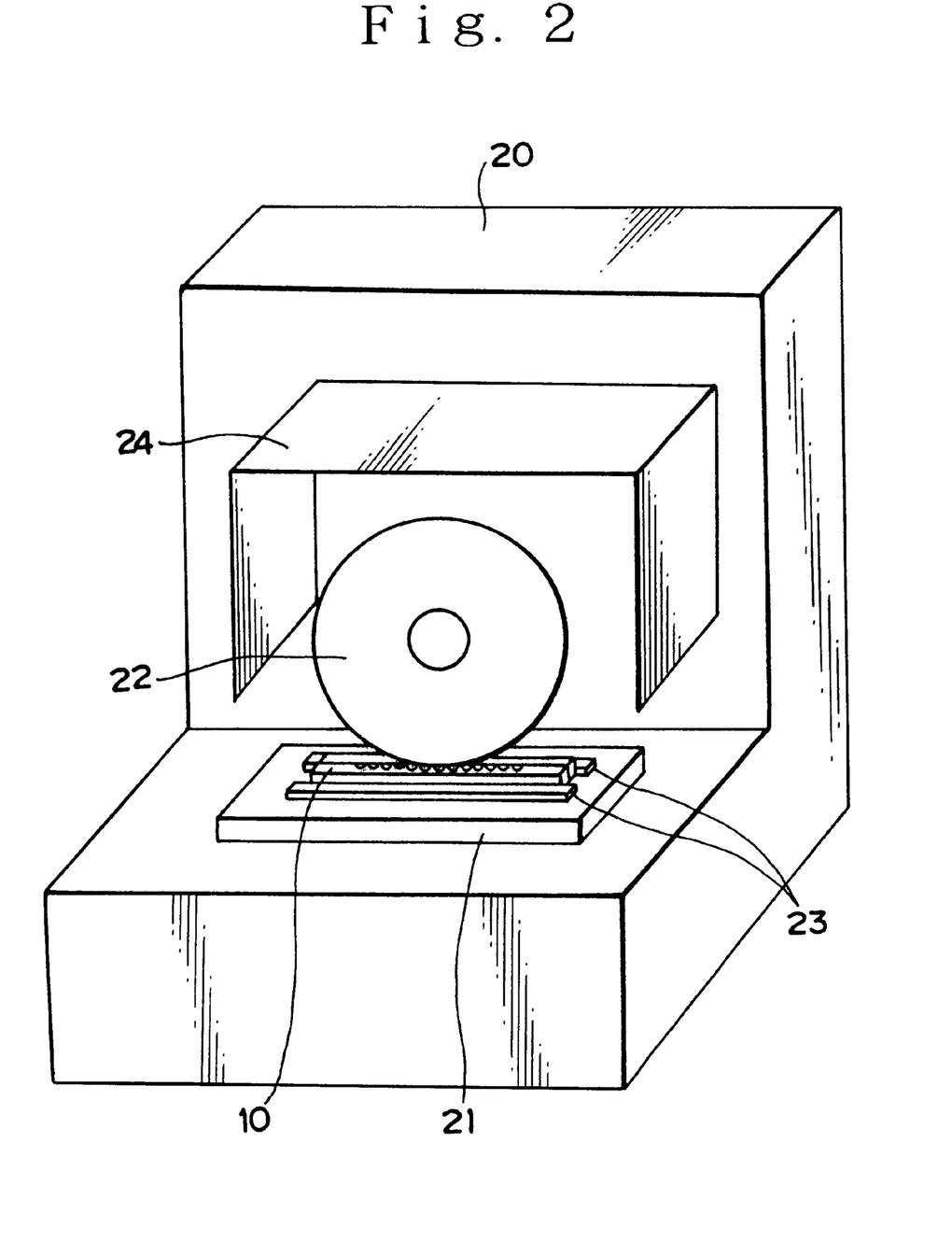
FIG. 2 shows a manner of cutting by a cutter in a perspective view.
Figure 3:
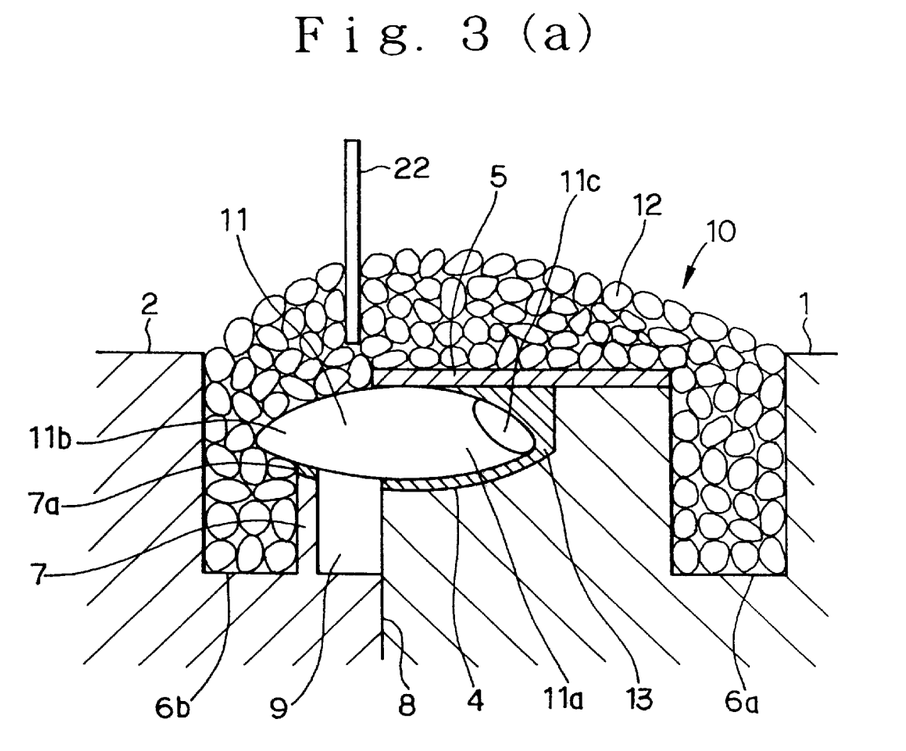
FIG. 3(a) shows a manner of cutting a material in a sectional view.
FIG. 3(b) shows a cut sample in a perspective view.

In FIG. 2, numerals denote: 20 a cutting arrangement, 21 a cutting stage, 22 a rotary cutter consisting of a diamond saw, 23 a fixing jig and 24 a cover.

The material preparation using the apparatus given above is performed in the manner as follows:

First, the material 11 is placed in the holder 4 on the holding unit 1 in a posture in which the side of its embryo 11c as the portion to be held 11a is put in the holder 4, as shown in FIG. 5(b) starting from the state as shown in FIG. 5(a), followed by filling up with a filler 13, such as a silicone putty, so as to cause the material 11 to be embedded therein and to be settled by the help of the settling means 5. Then, the mount 2 is connected by the joint means 3a, as shown in FIG. 3(a), whereupon the protruding portion 11b is affixed to the affixing means 7a and is caused to rest on the protruding portion support 7. In this state, the material preparation apparatus 10 is mounted on the cutting stage 21 of the cutting arrangement 20 and is fixed at a proper position by means of the fixing jig 23, as shown in FIG. 2. Dry ice 12 is then supplied to the dry ice wells 6a and 6b and also to the space above the material 11 to effect freezing of the material 11 with the gas phase replacement to thereby solidify the filler 13 to fix the material 11.

Then, the cutter 22 is put down to the cutting space 9 and the material is cut by moving either the cutter 22 or the cutting stage 21 to form a cut face 14 and a cut rift 15. Here, the frictional heat by the cutter 22 is absorbed by dry ice. Since the material 11 is made brittle by freezing, the portions of the materials cut off by the cutter 22 are fragmented and scattered away and the outer layer etc. of the material 11 will not adhere onto the cut face of the inner layer, so that the cut face 14 as an observation surface and the cut rift 15 remain without exhibiting deformation, destruction, denaturing or the like. By polishing the so-formed cut face shallowly by bringing down the cutter 22 again, a mirror-surface finishing can be attained.

Figure 4:
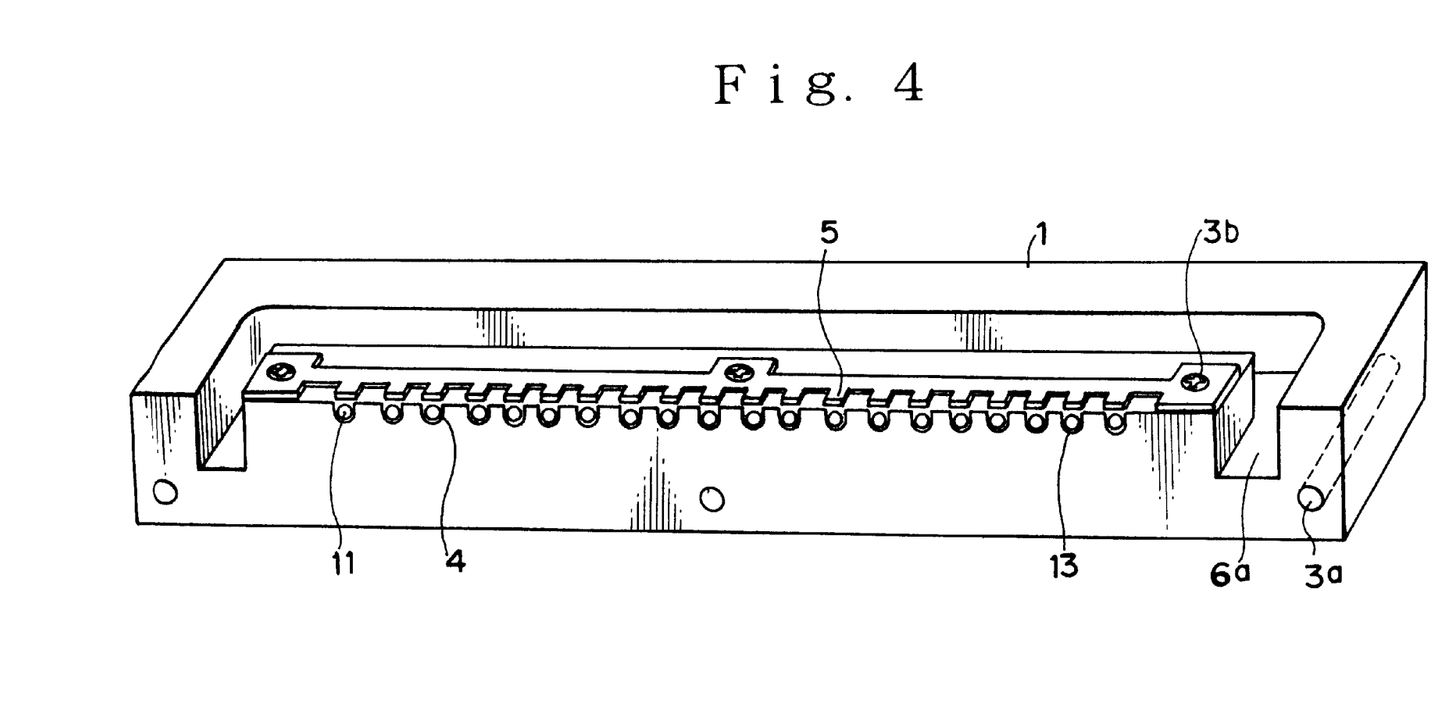
FIG. 4 shows the holding unit in a cut state in a perspective view.
Figure 5:
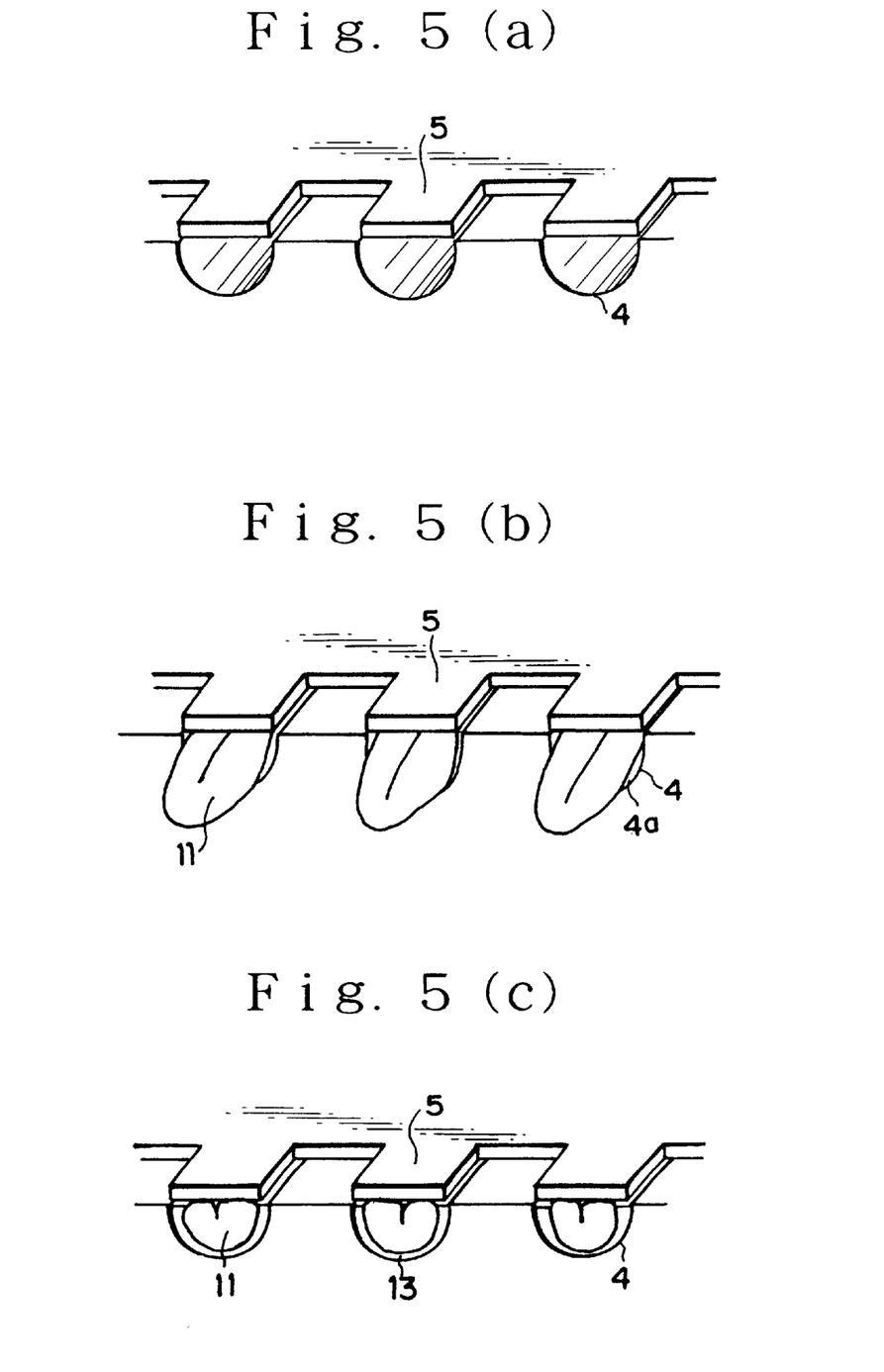
FIGS. 5(a), 5(b) and 5(c) show each the holding unit, each as a partial enlarged perspective illustration, in a state without a material, in a state holding the material and in a state with cut material, respectively.

The so-prepared material 11 is taken off from the mount 2 together with the holding unit 1 as shown in FIGS. 4 and 5(c), wherein the cut face 14 of the material 11 is in an exposed state. The form of the material 11 is as shown in FIG. 3(b). The material holder 1 is set on an analysis apparatus with the so-prepared materials 11 being in a frozen state as such or after having been warmed up to normal temperature for use as the sample for analysis etc. to carry out analysis etc. In the case of, for example, spectroanalysis, the holding unit 1 is mounted on the spectroanalysis apparatus in such a manner that the cut face 14 of the material 11 will be irradiated by a radiant ray. Here, the cut faces 14 are settled at a definite distance from the base of the holding unit 1 and at a definite angle (90°), so that it is possible to analyze a large number of samples under the same condition, permitting a high accuracy of the analysis. In the case of mass spectrometric analysis, a laser beam is projected onto a slice sample 16 formed between the cut face 14 and the cut rift 15 to cause thereby the substances of the sample to vaporize for the mass spectrometry. Other analyses, inspection, recording, observation and so on may also be carried out in a similar way as above. The protruding portion 11b cut off is recovered by being stickily captured on the affixing means 7a and is used for chemical analysis.

In the case of analyzing seeds of wheat, as in the above embodiment, one specific seed can be selected by the analysis as above and can be multiplicated using the embryo thereof by growing it. Here, the embryo 11c remains, keeping its germing ability, so that a plant can be grown from the embryo of the seed selected among them.

Below, the present invention is described by way of Examples.

EXAMPLE 1

Using a material preparation unit as shown in FIG. 1, samples were prepared from five seeds of each sort of wheat among Norin 61, Kanto 119, Halberd and Eradu (total 20 seeds) as the material by forming a cut face and a cut rift, which were analyzed for the whiteness of the seed by calorimetric analysis. The material preparation apparatus was made up by cutting an acrylic resin block. The sample holder was coupled with the mount by jointing screws to build up the preparation unit. On the holders, each coated with a putty based on silicone in a thin layer, the seeds of wheat were set in the holders, wherein each lower side thereof was embedded in the putty while installing by screwing a settling means constituted of a plate spring (t=1 mm) made of a stainless steel produced by a wire-cut spark erosion machine.

The wheat was cut using a high precision slicer (USM 150 A, supplied from Toshiba Machine Co., Ltd.) with its edible part, i.e. the endosperm part, constituting the protruding portion, in the manner as follows. The sample holder having 20 seeds was fixed on an electromagnetic chuck-provided stage of the slicer using a fixing jig under positioning of the position to be cut, whereupon dry ice crushed into particles of about 1 mm size was placed in the dry ice wells and over the materials to cool the entire assembly at −78.5° C. to freeze the materials and the putty to thereby prevent deformation and heating upon cutting, while replacing oxygen with the sublimed carbon dioxide gas to exclude oxidation. Cutting was carried out using a diamond saw (supplied from the firm Asahi Diamond, with $\phi$=100 mm, t=200 $\mu$m and diamond particle size =500 mesh) at a revolution rate of 6,000 r.p.m. to cut the sample placed under the dry ice powder. The resulting cut face was then shaven to a depth of 5–10 $\mu$m to finish into a mirror surface which served as the site of the sample to be examined. If uniformity of the thickness of the sample is required, a cut slit is formed behind the cut face at a position of 1 mm distant from the cut face to prepare for a constant thickness of the sample slice.

For determining the whiteness, the mount was disengaged from the material preparation unit having the row of cut seeds by turning the jointing screws and was settled on the material stage so that the mirror-finished cut face was on the upper side, whereupon a micrometer colorimetry on microsurfaces ($\phi$300 $\mu$m) was performed. The colorimetric data were entered in a computer and were analyzed by colored imaging under the use of a color-analyzing software. The results are given in Table 1.

TABLE 1

| Object | Norin 61 | Kanto 119 | Halberd | Eradu |
|---|---|---|---|---|
| Whiteness observed | 96.02 | 93.07 | 67.24 | 86.39 |
| | 71.45 | 84.71 | 83.68 | 96.08 |
| | 80.39 | 87.3 | 78.01 | 85.96 |
| | 72.87 | 98.85 | 76.28 | 93.6 |
| | 81.68 | 82.54 | 60.45 | 97.82 |
| Average | 80.48 | 89.29 | 73.13 | 91.97 |
| Standard error | 9.78 | 6.64 | 9.23 | 5.50 |

INDUSTRIAL APPLICABILITY

The process and the apparatus for the material preparation according to the present invention can be utilized for forming a cut face and/or a cut rift, so as to permit the use of a material subject to deformation, destruction or denaturing, such as biological, organic or chemical substance, for the sample for analysis, observation or recording and for other material.

What is claimed is:

1. A process for preparing a material to be analyzed, comprising the steps of:

holding the material in a holder of a holding unit;

fixing the material held in the holder by settling the material by a settling means;

covering the material with dry ice to effect the freezing thereof;

replacing an ambient gas phase with carbon dioxide gas evolved from the dry ice;

cutting the frozen material with a cutter to form a cut face and/or a cut rift and cut fragments; and scattering the cut fragments away from the cut face to avoid the contamination thereof.

2. The process as claimed in claim 1, wherein the material is embedded in a filler filled in the holding unit and the filler is solidified and frozen in this state by dry ice, before the material is cut by the cutter.

3. The process as claimed in claim 1, wherein the cut surface, resulting after the cut face and/or the cut rift is formed by the cutter, is polished by the cutter to attain a mirror surface finishing.

4. The process as claimed in claim 1, wherein the material is a sample for analysis, observation or recording.

5. A material prepared by the process as claimed in claim 1.

6. A method for effecting analysis of the material claimed in claim 5, comprising the steps of:

positioning the material provided with a cut face and/or a cut rift in a manner so that it can be analyzed by an analyzing apparatus; and effecting analysis on the cut face by the analyzing apparatus.

7. An apparatus for effecting material preparation comprising a holding unit having one or more holders, a settling means for settling a material held in the holder, dry ice wells disposed so as to effect freezing of the material held in the holding unit and to effect a gas phase replacement and a cutting space for permitting cutting of the material by a cutter in a state frozen by dry ice with a gas phase replacement to form a cut face and/or a cut rift.

8. The apparatus as claimed in claim 7, wherein a plurality of the holders are arranged in a row.

9. The apparatus as claimed in claim 7, wherein it further comprises a mount which has a support for supporting the protruding portion of the material protruding from the holding unit and which is disposed on the holding unit disengageably.

10. The apparatus as claimed in claim 9, wherein the mount has an affixing means for affixing the cut off protruding portion.

* * * * *